(12) United States Patent
Vaisnys et al.

(10) Patent No.: US 7,548,781 B2
(45) Date of Patent: Jun. 16, 2009

(54) ENVIRONMENTALLY RESPONSIVE ACTIVE STATUS INDICATOR SYSTEM AND METHOD

(75) Inventors: Gintaras A. Vaisnys, Guilford, CT (US); Giovanni C. Meier, Guilford, CT (US); Glenn W. Laub, Guilford, CT (US)

(73) Assignee: Defibtech, LLC, Guilford, CT (US)

( * ) Notice: Subject to any disclaimer, the term of this patent is extended or adjusted under 35 U.S.C. 154(b) by 630 days.

(21) Appl. No.: 11/386,057

(22) Filed: Mar. 21, 2006

(65) Prior Publication Data
US 2007/0078487 A1    Apr. 5, 2007

Related U.S. Application Data

(60) Provisional application No. 60/663,909, filed on Mar. 21, 2005.

(51) Int. Cl.
*A61N 1/39* (2006.01)
(52) U.S. Cl. ........................................................ 607/5
(58) Field of Classification Search ...................... 607/5
See application file for complete search history.

(56) References Cited

U.S. PATENT DOCUMENTS

| | | | |
|---|---|---|---|
| 4,101,787 A | 7/1978 | Vail | |
| 4,590,943 A | 5/1986 | Paull et al. | |
| 5,224,870 A | 7/1993 | Weaver et al. | |
| 5,314,451 A | 5/1994 | Mulier | |
| 5,350,317 A | 9/1994 | Weaver et al. | |
| 5,372,605 A | 12/1994 | Adams et al. | |
| 5,470,343 A | 11/1995 | Fincke et al. | |
| 5,483,165 A | 1/1996 | Cameron et al. | |
| 5,562,710 A | 10/1996 | Olsen et al. | |
| 5,579,234 A | 11/1996 | Wiley et al. | |
| 5,591,213 A | 1/1997 | Morgan et al. | |
| 5,593,426 A | 1/1997 | Morgan et al. | |
| 5,640,078 A | 6/1997 | Kou et al. | |
| 5,645,571 A | 7/1997 | Olson et al. | |
| 5,658,316 A | 8/1997 | Lamond et al. | |
| 5,697,955 A | 12/1997 | Stolte | |
| 5,700,281 A | 12/1997 | Brewer et al. | |
| 5,721,482 A | 2/1998 | Benvegar et al. | |
| 5,741,305 A | 4/1998 | Vincent et al. | |

(Continued)

OTHER PUBLICATIONS

Heartstream.RTM., Fore Runner.RTM. Semi-Automatic Defibrillator User's Guide, pp. 6-9 and 50, no date.

(Continued)

*Primary Examiner*—Carl H Layno
*Assistant Examiner*—Yun Haeng Lee
(74) *Attorney, Agent, or Firm*—King & Spalding LLP

(57) ABSTRACT

Battery powered systems with long standby times, such as automatic external defibrillators, may be required to indicate their operational status to a user by blinking lights or sounding speakers or buzzers. These active status indication activities consume power thereby reducing the battery life of the system. Automatically adjusting the level and frequency of these indication activities to match the ambient environment can reduce power consumption of the battery operated system. For example, in a dimly lit room, an indicator light may be visible even though it might be too dim to be seen in a bright room. Thus, if the room is dim, indicator lights can be dimmed to conserve power. These automatic adjustments made in response to the environment may help conserve power and extend battery life.

29 Claims, 8 Drawing Sheets

U.S. PATENT DOCUMENTS

| | | |
|---|---|---|
| 5,749,902 A | 5/1998 | Olson et al. |
| 5,773,961 A | 6/1998 | Cameron et al. |
| 5,782,878 A | 7/1998 | Morgan et al. |
| 5,791,907 A | 8/1998 | Ramshaw et al. |
| 5,792,190 A | 8/1998 | Olson et al. |
| 5,797,969 A | 8/1998 | Olson et al. |
| 5,800,460 A | 9/1998 | Powers et al. |
| 5,817,151 A | 10/1998 | Olson et al. |
| D405,754 S | 2/1999 | Barkley et al. |
| 5,868,790 A | 2/1999 | Vincent et al. |
| 5,868,794 A | 2/1999 | Barkley et al. |
| 5,879,374 A | 3/1999 | Powers et al. |
| 5,889,388 A | 3/1999 | Cameron et al. |
| 5,897,576 A | 4/1999 | Olson et al. |
| D409,752 S | 5/1999 | Bishay et al. |
| 5,904,707 A | 5/1999 | Ochs et al. |
| 5,913,685 A | 6/1999 | Hutchins |
| 5,919,212 A | 7/1999 | Olson et al. |
| 5,929,601 A | 7/1999 | Kaib et al. |
| 5,944,741 A | 8/1999 | Ochs et al. |
| 5,955,956 A | 9/1999 | Stendahl et al. |
| 5,964,786 A | 10/1999 | Ochs et al. |
| 5,983,137 A | 11/1999 | Yerkovich |
| 5,999,493 A | 12/1999 | Olson |
| 6,016,059 A | 1/2000 | Morgan |
| 6,021,352 A | 2/2000 | Christopherson et al. |
| 6,038,473 A | 3/2000 | Olson et al. |
| 6,075,345 A | 6/2000 | Lee |
| 6,101,413 A | 8/2000 | Olson et al. |
| 6,141,584 A | 10/2000 | Rockwell et al. |
| 6,148,233 A | 11/2000 | Owen et al. |
| 6,152,754 A | 11/2000 | Gerhardt et al. |
| 6,169,387 B1 | 1/2001 | Kaib |
| 6,201,992 B1 | 3/2001 | Freeman |
| 6,219,569 B1 | 4/2001 | Kelly et al. |
| 6,230,053 B1 | 5/2001 | Magin |
| 6,263,245 B1 | 7/2001 | Snell |
| 6,278,366 B1 | 8/2001 | Fletcher et al. |
| 6,301,502 B1 | 10/2001 | Owen et al. |
| 6,304,780 B1 | 10/2001 | Owen et al. |
| 6,314,320 B1 | 11/2001 | Powers et al. |
| 6,334,070 B1 | 12/2001 | Nova et al. |
| 6,363,282 B1 | 3/2002 | Nichols et al. |
| 6,366,809 B1 | 4/2002 | Olson et al. |
| 6,370,428 B1 | 4/2002 | Snyder et al. |
| 6,374,137 B1 | 4/2002 | Morgan et al. |
| 6,374,138 B1 | 4/2002 | Owen et al. |
| 6,381,492 B1 | 4/2002 | Rockwell et al. |
| 6,386,882 B1 | 5/2002 | Linberg |
| 6,397,104 B1 | 5/2002 | Miller et al. |
| 6,405,083 B1 | 6/2002 | Rockwell et al. |
| 6,418,342 B1 | 7/2002 | Owen et al. |
| 6,427,083 B1 | 7/2002 | Owen et al. |
| 6,438,417 B1 | 8/2002 | Rockwell et al. |
| 6,442,433 B1 | 8/2002 | Linberg |
| 6,480,745 B2 | 11/2002 | Nelson |
| 6,497,655 B1 | 12/2002 | Linberg et al. |
| 6,546,285 B1 | 4/2003 | Owen et al. |
| 6,586,850 B1 | 7/2003 | Powers |
| 6,597,948 B1 | 7/2003 | Rockwell et al. |
| 6,623,312 B2 | 9/2003 | Merry et al. |
| 6,648,823 B2 | 11/2003 | Thompson |
| 6,650,942 B2 | 11/2003 | Howard et al. |
| 6,671,545 B2 | 12/2003 | Fincke |
| 6,681,899 B1 | 1/2004 | Hong |
| 6,697,671 B1 | 2/2004 | Nova et al. |
| 6,754,538 B2 | 6/2004 | Linberg |
| 6,799,072 B2 | 9/2004 | Ries et al. |
| 6,820,998 B2 | 11/2004 | Chen |
| 6,878,112 B2 | 4/2005 | Linberg et al. |
| 6,920,360 B2 | 7/2005 | Lee et al. |
| 6,944,498 B2 | 9/2005 | Owen et al. |
| 6,955,864 B1 | 10/2005 | Vaisnys et al. |
| 6,978,182 B2 | 12/2005 | Mazar et al. |
| 6,990,371 B2 | 1/2006 | Powers et al. |
| 6,993,386 B2 | 1/2006 | Lin et al. |
| 2002/0032470 A1 | 3/2002 | Linberg et al. |
| 2002/0082644 A1 | 6/2002 | Picardo et al. |
| 2002/0095196 A1 | 7/2002 | Linberg et al. |
| 2003/0004547 A1 | 1/2003 | Owen et al. |
| 2003/0055460 A1 | 3/2003 | Owen et al. |
| 2003/0068914 A1 | 4/2003 | Merry et al. |
| 2003/0144711 A1 | 7/2003 | Pless et al. |
| 2003/0205988 A1 | 11/2003 | Vaisnys et al. |
| 2004/0059405 A1 | 3/2004 | White et al. |
| 2004/0122488 A1 | 6/2004 | Mazar et al. |
| 2004/0133244 A1 | 7/2004 | Vaisnys et al. |
| 2004/0143298 A1 | 7/2004 | Nova et al. |
| 2004/0215278 A1 | 10/2004 | Stegink et al. |
| 2005/0036294 A1 | 2/2005 | McMahon |
| 2005/0137653 A1 | 6/2005 | Friedman et al. |
| 2005/0159787 A1 | 7/2005 | Linberg et al. |
| 2005/0225983 A1 | 10/2005 | Fornell |
| 2005/0261742 A1 | 11/2005 | Nova et al. |

OTHER PUBLICATIONS

Hewlett Packard, 43110 A Defibrillator/Monitor Operating Guide, Eighth Edition, pp. 2, 5,, 36-39, Aug. 1991.

Agilent Heartstream FR2, M3860A, M3861A, User's Guide, pp. 2-1-2-2, 2-4, 4-5, and B6, 2000.

Medtronic Physio-Control, Lifepack.RTM. 500 automated external defibrillator, Service Manual, pp. 3 of 12-4-12, 7 of 12-10 of 12, 12 of 12, 2001.

Medtronic Physio-Control, Lifepak.RTM. 500 Automated External Defibrillator Operating Instructions, pp. 2-5-2-6, 5-7-5-11, 5-16-5-17, Mar. 2001.

Survivalink FirstSave.TM. Operation and Service Manual, pp. 20, 29-31, 65, 70,84 and 85, 2000.

Swerdlow et al., "Cardiovascular Collapse Caused by Electrocardiographically Silent 60-Hz Intracardiac Leakage Current", 1999, American Heart Association, pp. 1-13.

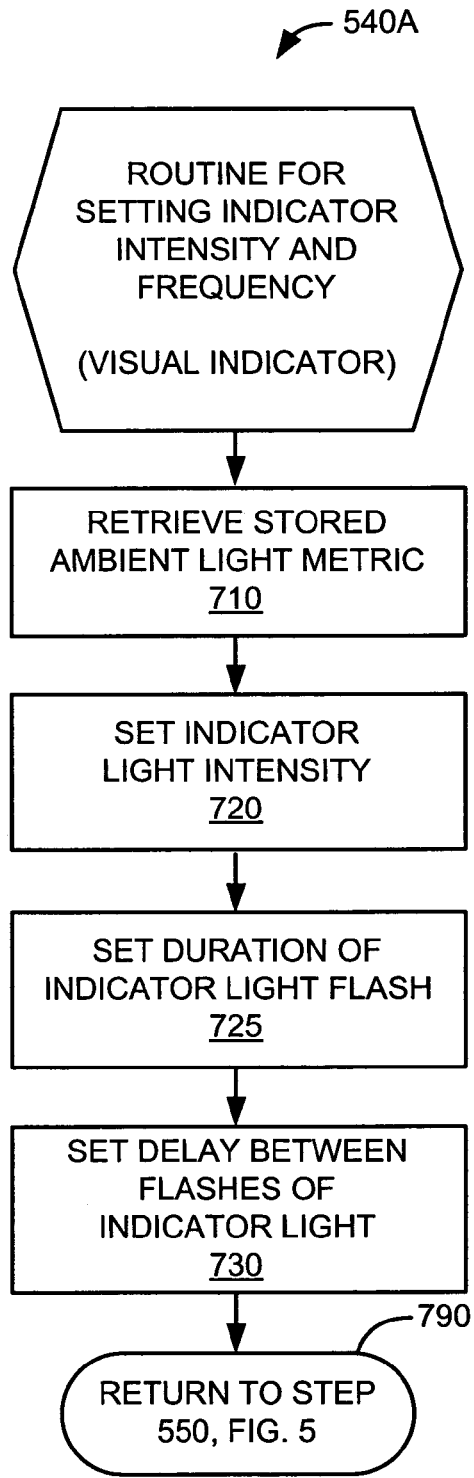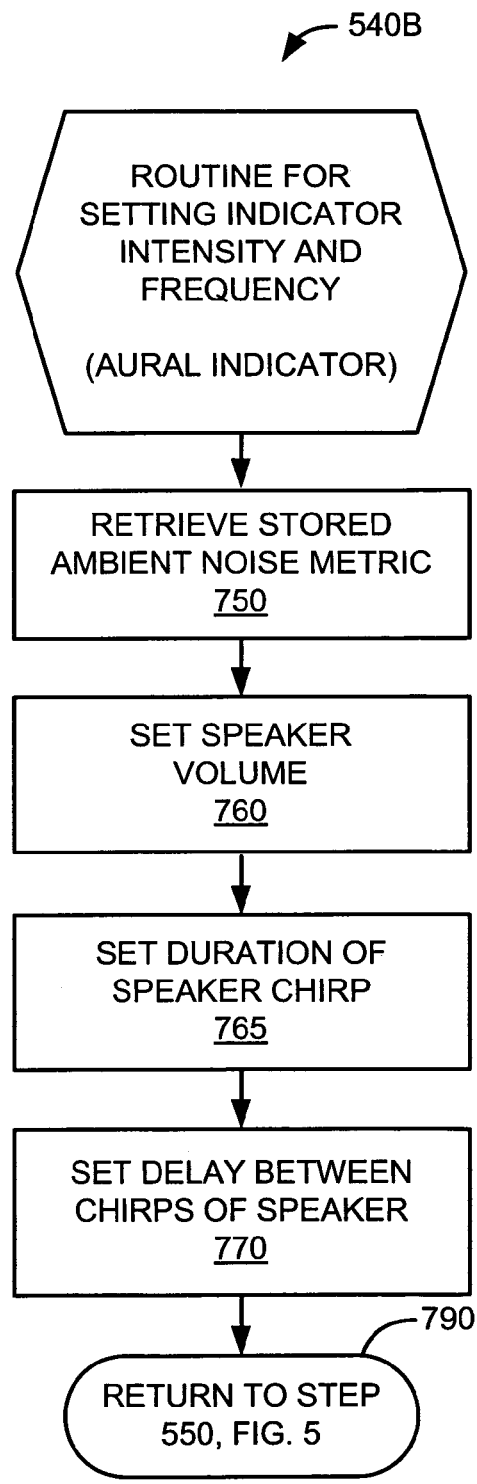
FIG. 7A
FIG. 7B

ENVIRONMENTALLY RESPONSIVE ACTIVE STATUS INDICATOR SYSTEM AND METHOD

PRIORITY CLAIM TO PROVISIONAL APPLICATION

This application claims priority to provisional patent application entitled, "Environmentally Responsive Active Status Indicator" filed on Mar. 21, 2005 and assigned U.S. Application Ser. No. 60/663,909. The entire contents of the provisional patent application mentioned above are hereby incorporated by reference.

TECHNICAL FIELD

The present invention is generally directed to battery-powered cardiac defibrillation systems, and relates more particularly to status indicators that conserve battery power by automatically adjusting their operation in response to their environment.

BACKGROUND OF THE INVENTION

Automatic external defibrillators (AEDs) are defibrillators that are designed to be operated by users with minimal training. Because AEDs can be used by non-medical personnel to treat sudden cardiac arrest (SCA), they are being deployed in a myriad of locations outside of traditional medical settings. As a result, more and more non-medical establishments are purchasing AEDs for deployment in their environments. AEDs are typically powered by stand alone battery systems.

AEDs are typically standby devices that are used infrequently and that remain in storage for long periods of time. This standby storage time can be on the order of months or even years. Minimizing power consumed by the AED while it is in standby mode during storage may extend the battery life of the system and reserve battery power for rescue attempts using the AED.

Since AEDs are in standby mode for long periods of time, knowing the operational status of a standby AED is very important. The operational status of an AED can be determined by various internal self tests. These tests may cover general operations, battery life, memories, software, etc. The results of these tests can be communicated to a user via visual or aural indicators even while the AED is in a low power standby mode. In such a system, there can be a status circuit or apparatus inside the AED that can report the status of the AED system. More generally, the AED may be referred to as the host system or host device. Various systems other than AEDs have similar low power consumption requirements for status indicators. Such systems may be referred to as host systems or host devices when they include status circuits that indicate the status of the host system.

Status indicators for host systems may be passive or active. An active indicator is one that may require power to be expended for it to continue to indicate, such as an indicator light. A passive indicator may continue to indicate without consuming additional power. For example, an indicator that mechanically changes colors by physically flipping an internal element that can be seen by a user through a window may be a passive indicator. Once the internal element of the passive indicator is physically flipped, it will stay in that state without additional power.

Active indicators can include lights, light emitting diodes (LEDs), video screens, speakers, or buzzers. Active indicators have the disadvantage of continuing to use power over time, but they can allow host status to be more readily determined in a wide variety of ambient conditions. For example, an active indicator may illuminate a green light to indicate that its battery is healthy, or a red light when its battery needs replacement. This repeated illumination of a light requires power, but may be much more likely to catch the attention of a user than a passive indicator would. This may be particularly true if the device is stored in a dark or low-visibility environment.

For battery powered, standby devices, such as AEDs, conservation of battery power is an important design goal. Such systems that use active status indicators have the additional challenge of reducing the amount of power they expend operating the status indicators. Since these devices may be stored, in standby mode, in a variety of environments there are times when the power used for status indication is excessive. For example, if a status light is designed to be bright enough to be seen in a well lit room, it may be much brighter than necessary when in a dark room or when stored in a cabinet, carrying case or car trunk.

Similarly for an aural status indicator, if the volume level of the indicator has adequate magnitude for a noisy environment, such magnitude may be much higher than necessary in a quiet room setting and therefore consume more power than necessary. Because of the importance of conserving battery life in systems with long standby requirements, such as AEDs, there is a need for status indicators that may sense their operating environment and then adjust accordingly either, or both, indicator intensity or indication event frequency.

SUMMARY OF THE INVENTION

The inventive active status indicator (ASI) system can indicate a status of a host device while the host device is in a non-operative state. The operation of the ASI system may automatically adjust indicators in response to sensing environmental conditions of the host device while the host device is in the non-operative state. A non-operative state of the host device usually includes situations in which the host device is performing less than all of its primary functions. For example, a non-operative state for automatic external defibrillators (AEDs) usually includes situations in which an AED is not performing a rescue on a patient. Functions that may occur during non-operative states in AEDs may include self-tests and active status indicator events.

The inventive ASI system may supply status information about the host device to a user. When the host device is operational, the ASI system may also supply the host device with environmental conditions sensed by the ASI system. The host device can query the ASI system for these parameters when the host device is in an operational state.

While the host device is in the non-operative state, the inventive ASI system can adjust the intensity level, duration of powering, or duration between powering, or any combination thereof, for status indication. These adjustments can reduce power consumed by the ASI system. Battery operated devices with long stand-by requirements, such as an automatic external defibrillator (AED), may benefit from increased battery life because of power conserving features of the inventive ASI system.

The inventive ASI system may also operate in a low power standby or sleep mode while the host device is also in a standby mode. However, the low power standby mode of the ASI system is different from the standby mode of the host device in that the ASI system can be "awakened" from its standby mode. Meanwhile, the host device becomes fully operational when it is switched from its standby mode or "off" mode.

The inventive ASI system can indicate the status of a host device by using illuminated indicators, indicator lights, audible speakers, or other outputs to a user. The intensity level of the indicator can be automatically adjusted to one that is appropriate for the environment. The inventive system can use light sensors, microphones, or other sensors to detect the environment and adjust the indicator accordingly. For example, the inventive ASI system may sense that a room is dark and then lower the brightness of an indicator light. In a brighter room, the inventive ASI system may increase the intensity of an indicator light so that it can still be seen.

In the case of an audible indicator, the inventive ASI system may sense the noise level in the room and then adjust the volume of the audible indicator output as needed. Supplying only the level of indication that a situation requires, may consume considerably less power than always supplying the maximum level of indication. This power savings can extend the battery life of battery-operated host devices.

The inventive ASI system may change the delay between indicator events in response to the environment. For example, if the room is extremely quiet, there might not be anyone present to see or hear an indicator event. Thus, the ASI may reduce power consumption by illuminating a light or chirping a speaker less frequently. Each illumination of the light or sounding of a speaker may be referred to as an indicator event.

The inventive ASI system may detect when the host device is enclosed, such as in a case, cabinet or car trunk and use this information to reduce the intensity or frequency of the status indicators. The ASI may cease indicator functions entirely in such environments. For host devices that are stored away until needed, this ASI functionality may significantly extend battery life. A common example of such a situation is an AED enclosed in a non-transparent or opaque, hard case where it is readily accessible during an emergency.

The inventive ASI system may detect when the host device is enclosed using a switch or magnetic detector. As an example of a magnetic detector, a reed switch in the host device may align with a magnet affixed to the case or enclosure. This can indicate to the inventive ASI system that the host device is in a specific environmental situation and indicator outputs should be adjusted accordingly. For example, if the host device is stored in an opaque carrying case, there may be no need to illuminate any indicator lights. Ceasing or reducing indicator events which might be unnecessary can significantly extend battery life of the host device.

The inventive ASI system may use reflections to detect when the host device is enclosed. If a large enough percentage of the light emitting from an indicator light of the host device is reflected right back into the light sensor of the host device, there may be a high likelihood that a cabinet or enclosure wall just outside the host device is providing a reflective surface. This capability may be used by the inventive ASI system to reduce or cease the indicator events and thus conserve power.

In addition to reacting to environmental conditions, the inventive ASI system may also adjust indicators in response to internal events of the host device. The ASI system may reduce indicator intensity levels, duration of powering for an indicator, and increase delays between indicator events if a battery level of the host device is below a certain threshold. In such situations, the host device can detect low battery power status during normal operations and set a flag that can be checked by the ASI system. The ASI can adjust indicator operations in response to this flag in order to prevent rapid discharge of the remaining battery power.

The inventive ASI system, according to another exemplary aspect, may not detect environmental conditions every time a status indicating event is scheduled to occur. That is, the inventive ASI system can detect environmental conditions such as ambient light conditions or ambient acoustic noise conditions at a rate that can be different than a rate set for an indicating event.

BRIEF DESCRIPTION OF THE DRAWINGS

FIG. 7A is a logic flow diagram illustrating an exemplary routine for setting the indicator intensity and frequency in a system with a visual ASI that is environmentally responsive according to one exemplary embodiment of the invention.

FIG. 7B is a logic flow diagram illustrating an exemplary routine for setting the indicator intensity and frequency in a system with an auditory ASI that is environmentally responsive according to one exemplary embodiment of the invention.

DETAILED DESCRIPTION OF EXEMPLARY EMBODIMENTS

The inventive ASI system may comprise an active status indicator (ASI) whose operation is automatically adjusted in response to its environment while the host device is in a non-operative state. The inventive ASI system may supply status information about a host device to a user while the host device is in a non-operative state. The inventive ASI system may adjust the intensity level, duration of powering, or duration between powering of any status indication in response to the ambient environment of the host system. Such adjustments may reduce power consumed by the ASI system thereby extending battery life of the ASI system and the host device.

The inventive ASI system may indicate the status of a host device using illuminated indicators, indicator lights, audible speakers, or other outputs to a user. The intensity level, duration of powering, or duration between powering, or any combination thereof, of the indicators may be automatically adjusted to one that is appropriate for the environment. The inventive system may use light sensors, microphones, or other sensors to detect the environment and adjust the indicator accordingly.

The inventive system may comprise an ASI processor which may comprise a microcontroller with a low-power sleep mode for sensing the environment and controlling the active indicators accordingly. The inventive ASI system is designed to substantially minimize or eliminate all activity and power consumption during its sleep mode. The ASI processor may also be used to support other functions of the host system such as an on/off switch response, self test operations, or controlling the operational state of the host systems main processor.

The inventive ASI system may use reflections of its own status indicators to determine when the host system in physically enclosed. The level of light or sound from an indicator that is reflected back to the host may be an indication of the host system being physically enclosed. Such an indication may be used to further reduce, or possibly disable, any power dedicated to driving active status indicators.

Figure 1:
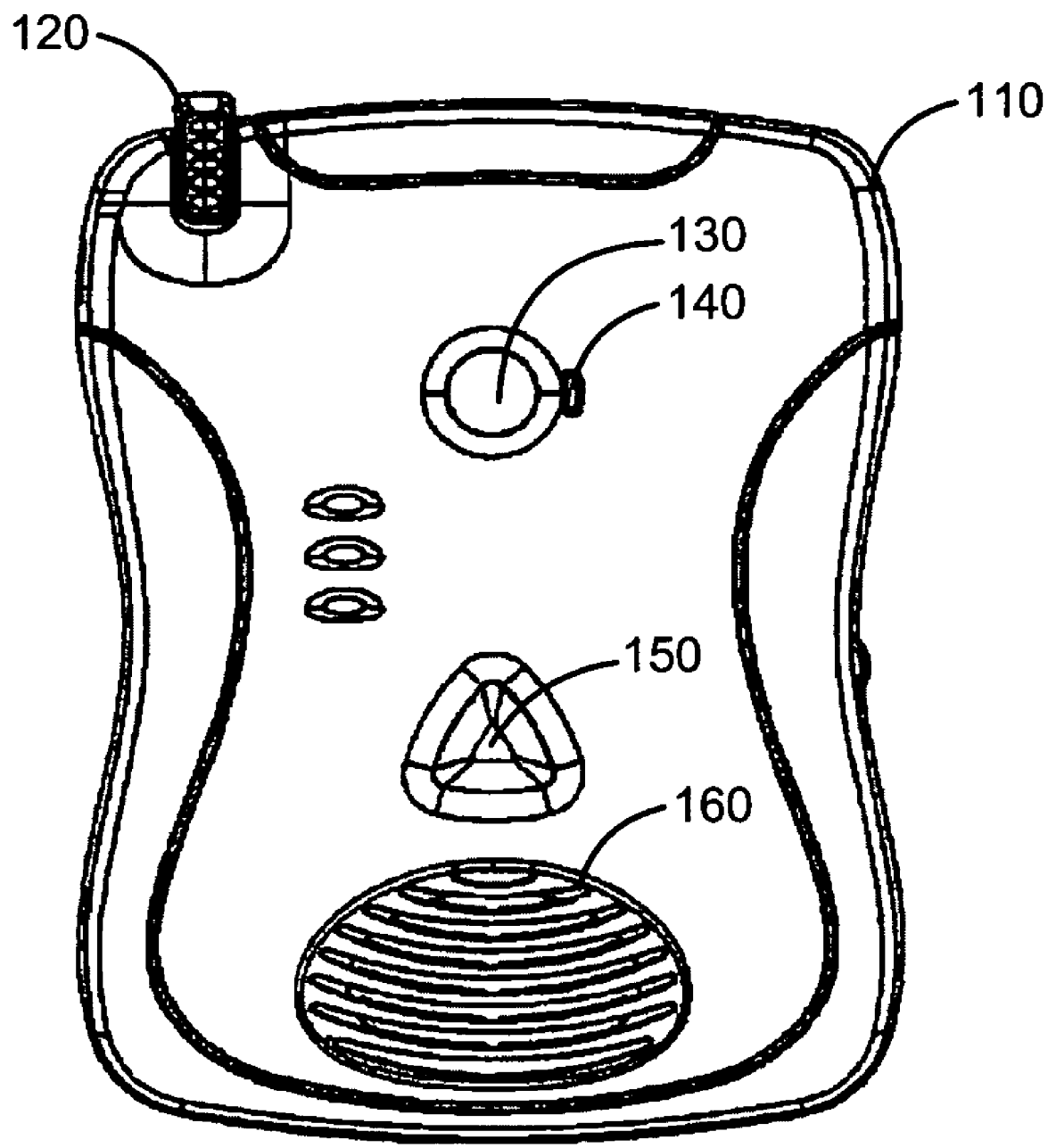
FIG. 1 illustrates a plan view of an AED according to one exemplary embodiment of the invention.

Turning now to the drawings, in which like reference numerals refer to like elements, FIG. 1 illustrates a plan view of an AED 100 with an environmentally responsive ASI system according to one exemplary embodiment of the invention. Even while AED 100 is in standby mode, light-pipe 140 can be illuminated by LED 235 (see FIG. 2) which may serve as an active status indicator (ASI) for AED 100. Speaker 160 may also provide active status indication. Additionally, speaker 160 may provide instructions or other information. Connector 120 can connect patient electrodes (see FIG. 1) to AED 100.

The patient electrodes can be used to monitor ECG information from a patient to determine if the patient's cardiac rhythm is suitable for defibrillation shock. If so, the operator may be instructed to press button 150 to initiate an electrical shock through the patient electrodes attached at connector 120. The outer housing 110 of AED 100 may contain and protect the electronic components of AED 100 including ASI circuit 200 (see FIG. 2).

An on/off button 130 can be used to power AED 100 into an operational mode or transition AED 100 into standby mode. While the on/off button 130 appears to the user to turn off AED 100 completely, the on/off button 130 may actually turn off power to a host processor 410 (See FIG. 4) while placing an ASI processor 210 (See FIG. 4) into its very low power sleep mode or standby mode.

Figure 2:
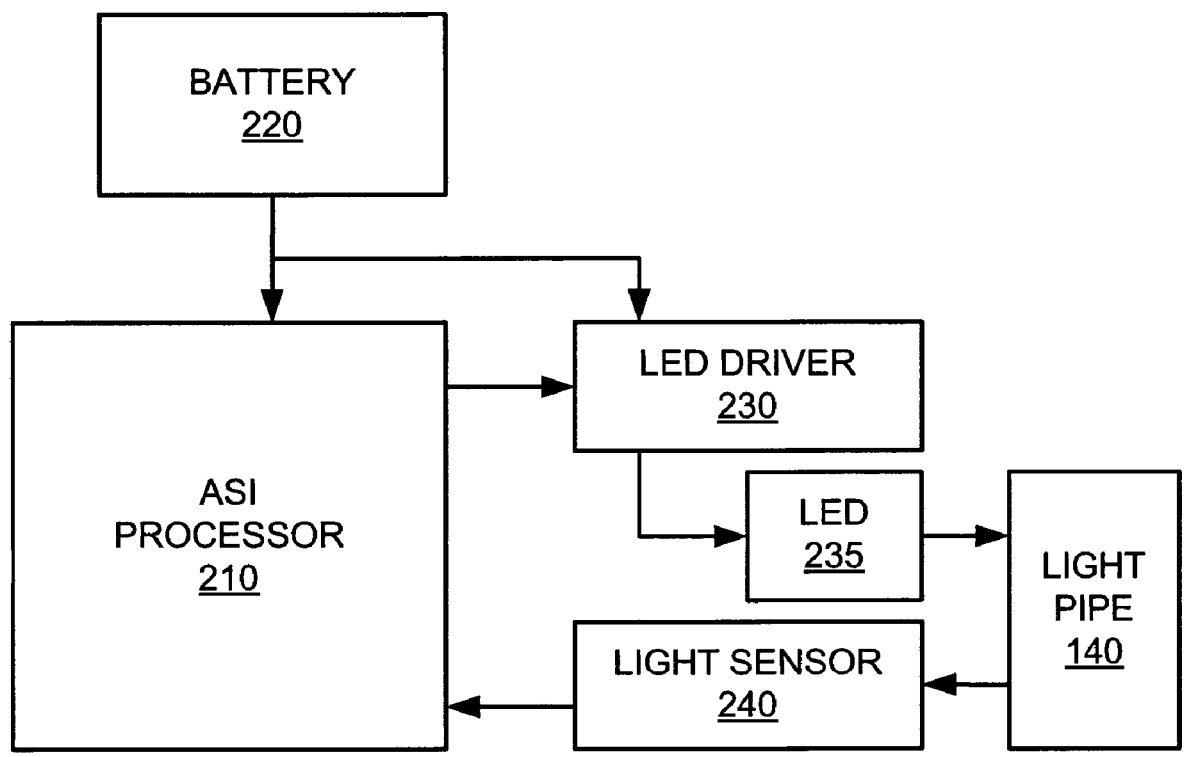
FIG. 2 is a functional block diagram illustrating the ASI processor and an environmentally responsive LED indicator according to one exemplary embodiment of the invention.

Referring now to FIG. 2 which illustrates a functional block diagram of an environmentally responsive ASI circuit 200 according to one exemplary embodiment of the invention, an LED light 235 is used as an active visual indicator. ASI processor 210 may comprise a general processor such as the MSP430F1232, an ultra-low-power microcontroller, made by Texas Instruments. However, one of ordinary skill in the art will appreciate that ASI processor 210 may comprise a microcontroller, microprocessor, DSP processor, application specific logic, programmable logic, or numerous other forms without departing from the spirit and scope of the invention. Battery 220 powers the ASI circuit 200. ASI processor 210 may spend most of the time in a low-power sleep mode. Timers (not illustrated), which may be internal or external to processor 210, wake processor 210 every few seconds to allow it to briefly illuminate LED 235 thereby providing a status indication.

Prior to illuminating LED 235, ASI processor 210 samples light sensor 240 to determine the ambient light level around the host device. LED driver 230 can control the intensity, or brightness, level of LED 235. LED driver 230 may control this intensity using a pulse width modulation (PWM) technique when driving LED 235. ASI Processor 210 sets this intensity level based on ambient light levels sampled from sensor 240. Light pipe 140 may be a translucent plastic element that optically couples LED 235 and light sensor 240 to the outside of system housing 110. An exemplary application of the inventive ASI system can comprise the periodic illumination of LED 235 in a green state to indicate that the host system is operating properly and further comprise changing the illumination state of LED 235 to red if the host system requires operator attention. Operator attention may be required, for example, because of a failed internal self test or a low charge detected on battery 220.

Figure 3:
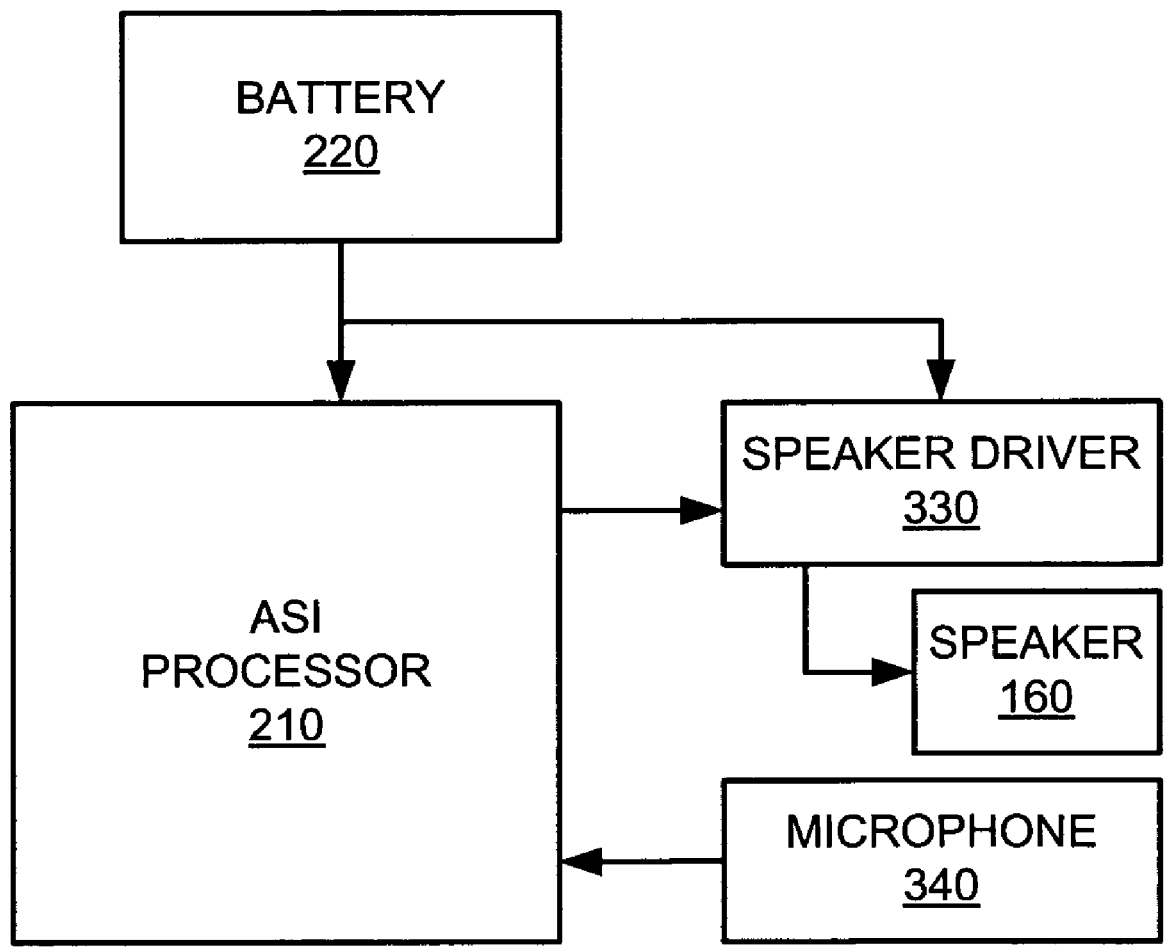
FIG. 3 is a functional block diagram illustrating the ASI processor and an environmentally responsive audible indicator according to one exemplary embodiment of the invention.

Referring now to FIG. 3 which illustrates a functional block diagram of an environmentally responsive ASI circuit 300 according to one exemplary embodiment of the invention, sound from a speaker 160 is used as an active, aural indicator. Battery 220 powers the ASI circuit 200. ASI processor 210 may spend most of the time in a low-power sleep mode. Timers (not illustrated), which may be internal or external to processor 210, wake processor 210 every few seconds to allow it to sound speaker 160 thereby providing a status indication. Prior to sounding speaker 160, ASI processor 210 samples microphone 340 to determine the ambient noise level around the host device. Speaker driver 330 can control the volume, or loudness, of speaker 160. Processor 210 sets this volume level based on ambient noise levels sampled from microphone 340.

Figure 4:
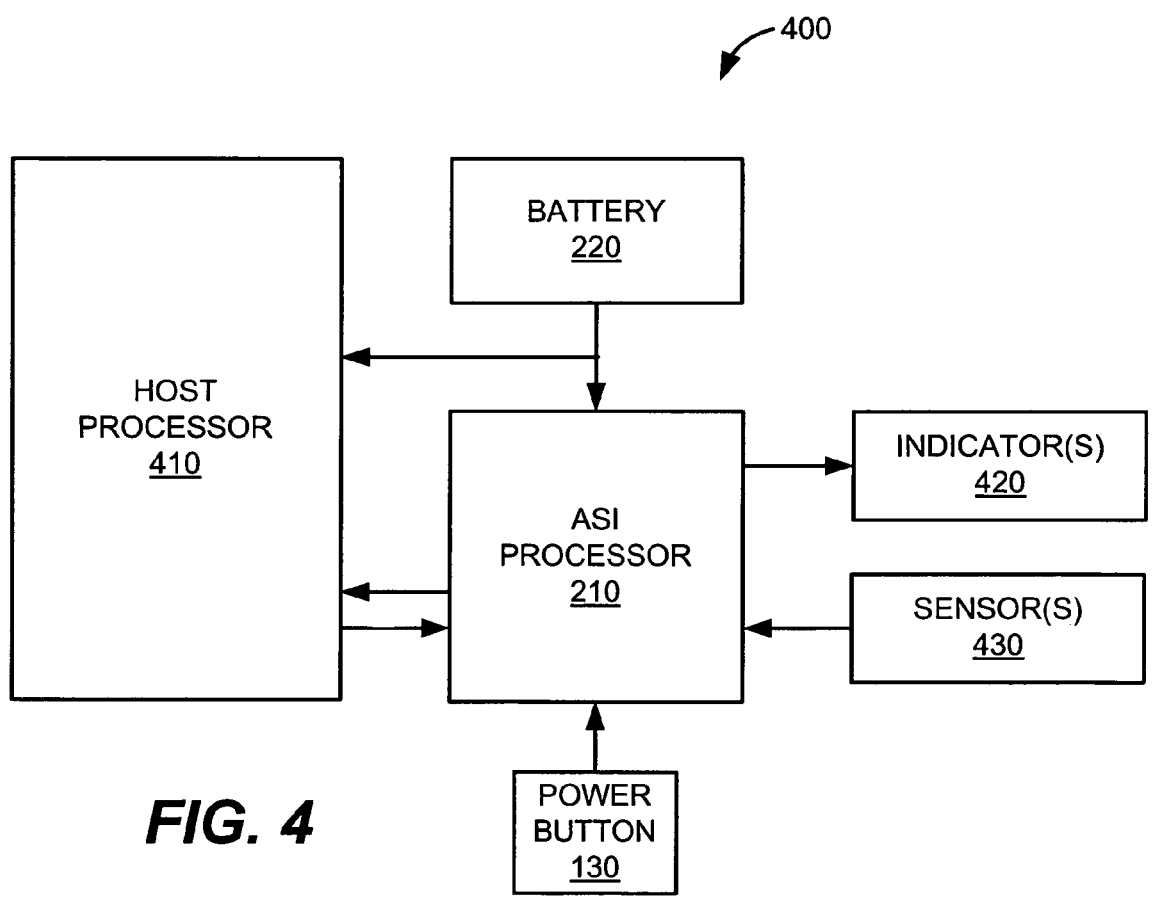
FIG. 4 is a functional block diagram illustrating the relationship between the ASI processor and the host processor according to one exemplary embodiment of the invention.

Referring now to FIG. 4 which illustrates a functional block diagram 400 illustrating a relationship between ASI processor 210 and host processor 410. Battery 220 powers the system, including both processors 210 and 410. ASI processor 210, which may spend most of the time in a low-power sleep mode, wakes every few seconds to sample sensors 430 and actuate indicators 420. ASI processor 210 may also wake periodically to perform, or cause to be performed, built in self tests of the host system. ASI processor 210 may also monitor power button 130 in order to turn host processor 410 on and off. Sensors 430 may comprise light sensor 240 (see FIG. 2) and also may comprise microphone 340 (see FIG. 3). Indicators 420 may comprise LED 235 (see FIG. 2) and may also comprise speaker 160 (see FIG. 3).

Figure 5:
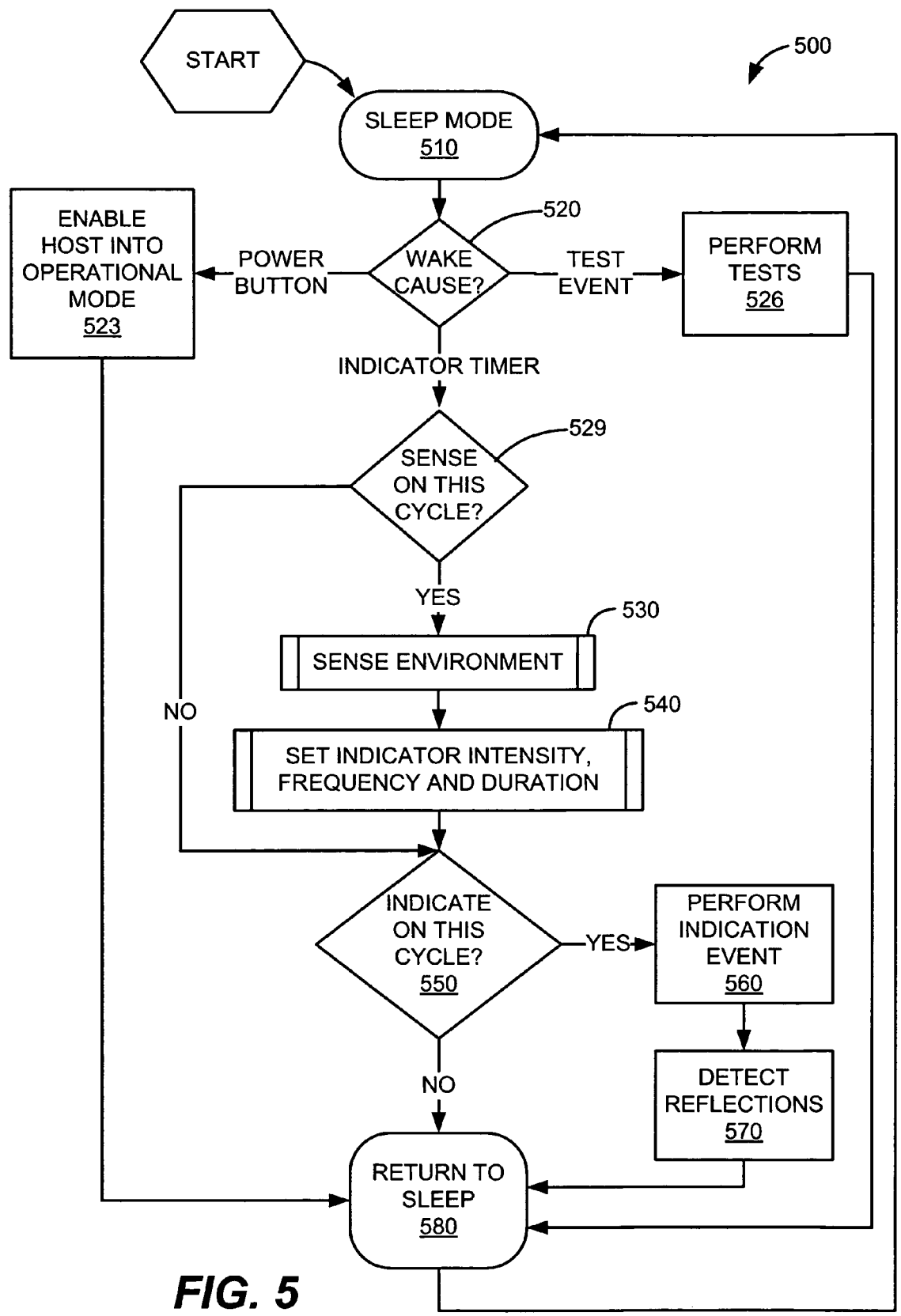
FIG. 5 is a logic flow diagram highlighting exemplary steps for an ASI processor in a system with environmentally responsive active status indicators according to one exemplary embodiment of the invention.

FIG. 5 illustrates a logical flow diagram 500 of a method for reducing power consumption by an active status indicator (ASI) and extending battery life for a host system. Logical flow diagram 500 highlights some key functional features of ASI processor 210. One of ordinary skill in the art will appreciate that process functions of ASI processor 210 may comprise firmware code executing on a microcontroller, microprocessor, or DSP processor; state machines implemented in application specific or programmable logic; or numerous other forms without departing from the spirit and scope of the invention. In other words, the invention may be provided as a computer program which may include a machine-readable medium having stored thereon instructions which may be used to program a computer (or other electronic devices) to perform a process according to the invention.

The machine-readable medium may include, but is not limited to, floppy diskettes, optical disks, CD-ROMs, and magneto-optical disks, ROMs, RAMs, EPROMs, EEPROMs, magnet or optical cards, flash memory, or other type of media/machine-readable medium suitable for storing electronic instructions.

Certain steps in the processes or process flow described in all of the logic flow diagrams referred to below must naturally precede others for the invention to function as described. However, the invention is not limited to the order of the steps described if such order or sequence does not alter the functionality of the present invention. That is, it is recognized that some steps may be performed before, after, or in parallel other steps without departing from the scope and spirit of the present invention.

Further, one of ordinary skill in programming would be able to write such a computer program or identify the appropriate hardware circuits to implement the disclosed invention without difficulty based on the flow charts and associated description in the application text, for example. Therefore, disclosure of a particular set of program code instructions or detailed hardware devices is not considered necessary for an adequate understanding of how to make and use the invention. The inventive functionality of the claimed computer implemented processes will be explained in more detail in the following description in conjunction with the remaining Figures illustrating other process flows.

Step 510 is a waiting step. ASI processor 210 can operate by predominantly waiting in a power saving sleep mode to be woken by events that it acts upon briefly before returning to the sleep mode. In the exemplary embodiment of the method illustrated in FIG. 5, three events may wake ASI processor 210 from its sleep mode. These events include, but are not limited to, a power button event, an indicator timer event, or a self test event. After handling whichever event awakens ASI processor 210 from the sleep mode of step 510, the ASI processor 210 can transition back through step 580 into the sleep mode of step 510 where ASI processor 210 waits for the next wake event.

In decision step 520, ASI processor 210 determines what type of event woke it from sleep mode. If the wake event was power button 130 being pressed, the ASI processor 210 performs step 523 enabling host processor 410 into its operational mode. In operational mode, host processor 410 is powered on to perform the main operations of the host system. For example, when the host system is AED 100, the main operations comprise patient heart rhythm analysis and possible delivery of defibrillation shocks to the patient. After enabling the host processor 410 into operational mode, ASI processor 210 may continue its operation according to the method 500 in parallel to operational functions of the host processor 410. However, host processor 410, while in its operational mode, may preempt use of indicators 420 or sensors 430 for operational functions. As examples, while in operational mode, host processor 410 may use speaker 160 to provide instructions to the operator, or microphone 340 to record audio of the rescue attempt.

During step 523, the host processor 410 may also query the ASI processor 210 for the environmental conditions of the AED 100 that are sensed by the ASI processor 210. The host processor 410 can use these environmental conditions sensed by the ASI processor 210 to adjust intensity level, duration of powering, or duration between powering of its operational indicators such as a speaker 160 or a LED 235.

If the wake event determined in step 520 is a test event, ASI processor 210 transitions to step 526 where internal self tests are initiated by ASI processor 210 and performed by ASI processor 210, host processor 410, or other system circuitry. A test event may be caused by a periodic test timer, a user request, or an external event such as the insertion of a new battery. Once self tests are completed, ASI processor 210 transitions from testing step 526 into step 580 where ASI processor 210 returns to sleep mode of step 510.

If the wake event determined in step 520 is an indicator timer, ASI processor 210 transitions to decision step 529 where it is determined if the ambient environment should be sensed on this timer cycle. In a preferred, yet exemplary embodiment, the ambient environment is sensed less frequently than the indicator is powered. That is, the inventive ASI system may not detect environmental conditions every time a status indicating event is scheduled to occur. The inventive ASI system can detect environmental conditions such as ambient light conditions or ambient acoustic noise conditions at a rate that can be different than the frequency set for an indicating event. That is, the environment may be sensed more or less frequently than the indicator is powered. One of ordinary skill in the art will appreciate that such alternate embodiments of the inventive method do not depart from the spirit or scope of the invention.

If it is determined during decision step 529 that the ambient environment is to be sensed, ASI processor 210 transitions to routine 530 where the ambient environment is sensed and then to routine 540 where the intensity, duration, and frequency of indicators are set according to ambient conditions sensed in routine 530. Further details of routines 530 and 540 will be discussed below with respect to FIGS. 6 and 7. If it is determined during decision step 529 instead that the ambient environment is not to be sensed during this timer cycle, the ASI processor 210 transitions directly to step 550.

In decision step 550, ASI processor 210 determines if an indicator event should be performed during the current indicator timer cycle or not. This feature allows the ASI system to slow down the rate of indicator events by skipping indicator cycles. One of ordinary skill in the art will appreciate that this same effect may be achieved by modifying the duration of the indicator timer used to wake the ASI processor 210 from sleep mode 510 into step 530. If no indicator event is to be performed during a specific cycle, ASI processor 210 transitions from decision step 550 into step 580 where ASI processor 210 returns to sleep mode of step 510.

In step 560, ASI processor 210 performs the indicator event. This indication may comprise flashing LED 235, or sounding speaker 160, or some other type of active status indication.

In step 570, ASI processor 210 may analyze indicator reflections to determine if the host system is currently enclosed. Using light sensor 240 to measure the proportion of light emitted by indicator 235 that is reflected directly back into the host system, the ASI processor may determine that there is an enclosure or cover surface immediately outside the host system housing 110. ASI processor 210 may respond to the presence of this surface as an indication that the host system is enclosed and therefore slow or cease visual status indication. Similarly, reflections or echoes of an aural indicator, such as speaker 160, may be detected using microphone 340. These echoes may likewise indicate the presence of an enclosure or cover surface outside the host system.

After step 570, the ASI processor 210 returns to its sleep mode in step 580 in which the host device is in a non-operative state. As noted previously, a non-operative state of the host device usually includes situations in which the host device is performing less than all of its primary functions. For example, a non-operative state for automatic external defibrillators (AEDs) usually includes situations in which an AED is not performing a rescue on a patient. Functions that may occur during non-operative states in AEDs may include self-tests and active status indicator events performed by ASI processor 210.

Figure 6A:
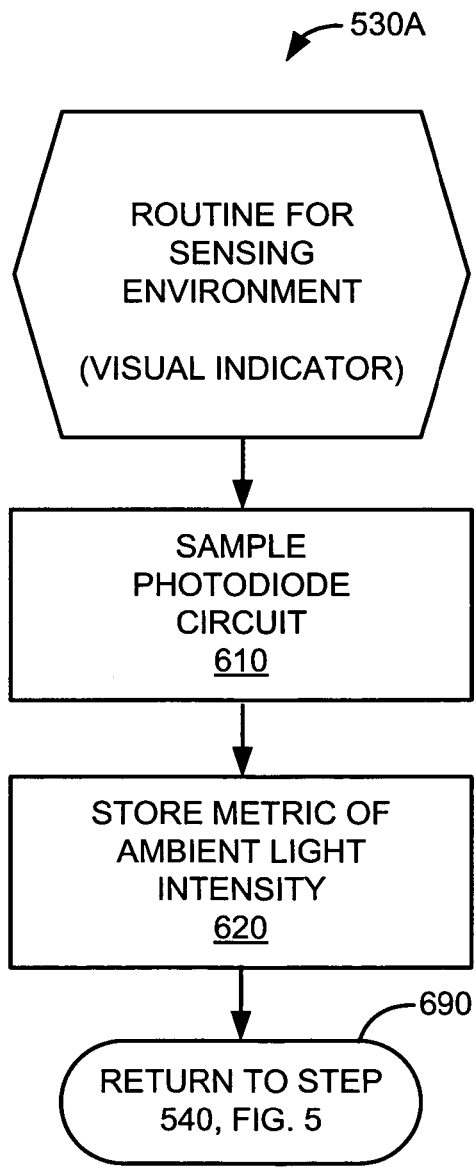
FIG. 6A is a logic flow diagram illustrating an exemplary routine for sensing the environment in a system with a visual ASI that is environmentally responsive according to one exemplary embodiment of the invention.

Referring now to FIG. 6A, a logical flow diagram of routine 530 illustrates the process of sensing ambient environment in an environmentally responsive ASI system with visual indication. In step 610, ASI processor 210 samples photodiode light sensor 240. In step 620, ASI processor 210 stores a measure of the ambient light intensity, or brightness, around the host system using the sampled data from step 610. This stored measure is used later in routine 540. Finally, in step 690, the routine 530 returns to the main process 500 illustrated in FIG. 5.

Figure 6B:
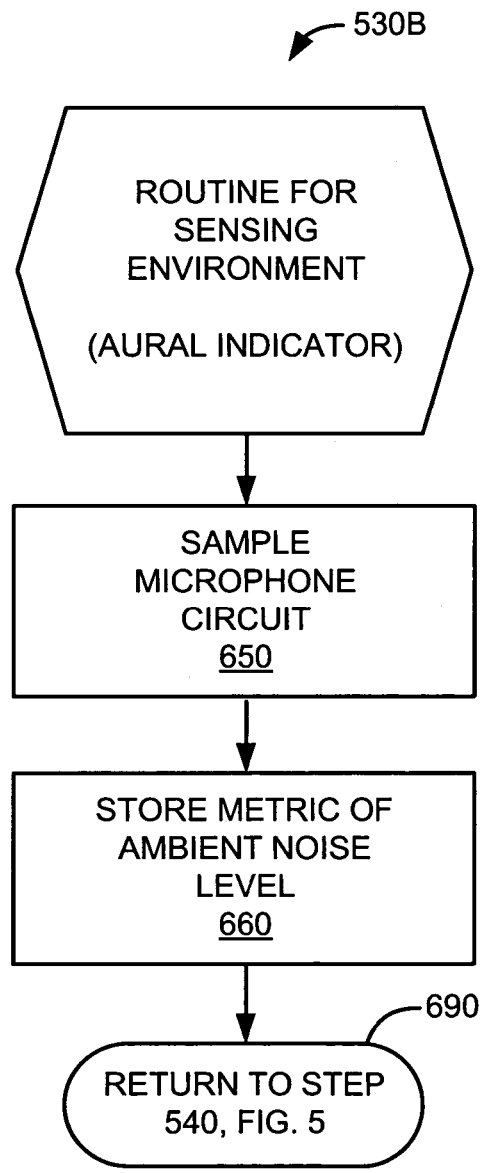
FIG. 6B is a logic flow diagram illustrating an exemplary routine for sensing the environment in a system with an auditory ASI that is environmentally responsive according to one exemplary embodiment of the invention.

Referring now to FIG. 6B, a logical flow diagram of routine 530 is illustrated for sensing the ambient environment in an environmentally responsive ASI system with aural indication. In step 650, ASI processor 210 samples microphone 340. In step 660, ASI processor 210 stores a measure of the ambient sound intensity, or loudness, around the host system using the sampled data from step 650. This stored measure is used later in routine 540. Finally, in step 690, the routine 530 returns to the main process 500 illustrated in FIG. 5.

Referring now to FIG. 7A, a logical flow diagram of routine 540 is illustrated for setting indicator intensity and frequency in an environmentally responsive ASI system with visual indication 235. In step 710, ASI processor 210 retrieves the stored measure of ambient light intensity from the stored value that was calculated by routine 530. In step 720, ASI processor 210 sets the intensity to be used when flashing the light indicator 235. This setting is made based on the ambient light intensity retrieved in step 710. For example, if the ambient lighting is dim, the ASI processor 210 may set the indicator light 235 intensity to a lower level or if ambient lighting is bright, ASI processor may set indicator light 235 intensity to a higher level.

In addition to these two relative examples of higher and lower light intensities, there may be many levels of intensity available to be set according to many different ambient brightness levels that may be sensed. Indicator brightness levels may be computed from the measured ambient light intensities, or alternatively, value ranges stored in one or more tables present in memory may be used to map measured ambient light intensities to appropriate indicator brightness levels. In step 725, ASI processor 210 sets the duration for powering indicator light 235 to create a flash. In step 730, ASI processor 210 sets the delay between illuminations of the indicator light 235. This feature may save battery power 220 by slowing the flashing of the indicator light 235. Finally, in step 790, the routine 540 returns to the main process 500 illustrated in FIG. 5.

Referring now to FIG. 7B, a logical flow diagram of routine 540 is illustrated for setting indicator intensity and frequency in an environmentally responsive ASI system with aural indication via speaker 160. In step 750, ASI processor 210 retrieves the stored measure of ambient sound intensity from the stored value that was calculated by routine 530. In step 760, ASI processor 210 sets the intensity, or volume, to be used when sounding speaker 160 as a status indicator. This setting is made based on the ambient sound intensity retrieved in step 750. For example, if the ambient sound level is high, the ASI processor 210 may set the volume of speaker 160 to a higher level so that it can be heard over the ambient noise.

If the ambient noise level is low, the ASI processor 210 may set the volume of speaker 160 to a lower level. In addition to these two relative examples of higher and lower speaker volume, there may be many levels of volume available to be set according to many different ambient noise levels that may be sensed. Speaker volume levels may be computed from the measured ambient noise intensities, or alternatively, value ranges stored in one or more tables present in memory may be used to map measured ambient noise levels to appropriate speaker volume levels. In step 765, ASI processor sets the duration for sounding speaker 160 during a speaker chirp. In step 770, ASI processor sets the delay between soundings of speaker 160. This feature may save battery power 220 by reducing the amount of energy used in sounding speaker 160 over a given period of time. Finally, in step 790, the routine 540 returns to the main process 500 illustrated in FIG. 5. In addition to the functionally of routine 540 setting the volume of speaker 160 for status indication purposes, the host processor 410 may retain these volume settings for speaker 160 during operational mode where it may use speaker 160 to provide instructions or other audio to the operator.

Figure 8:
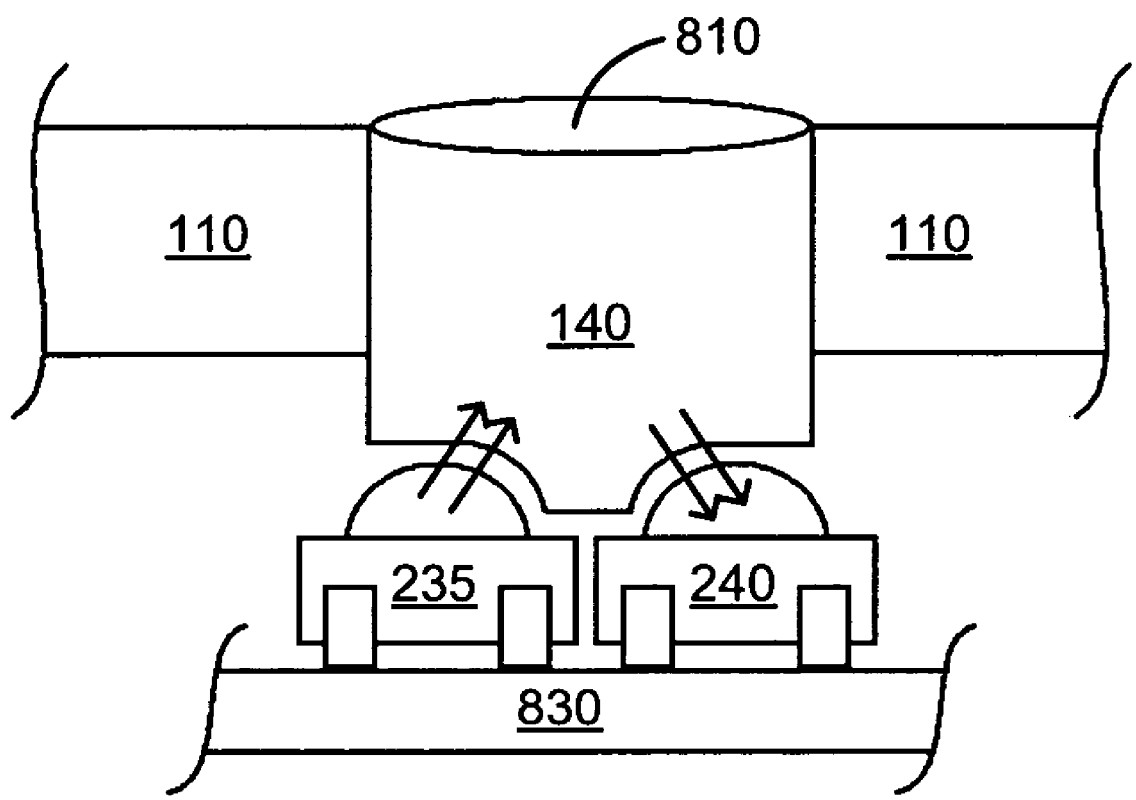
FIG. 8 is an elevation view illustrating a surface-mounted LED and surface-mounted photodiode both optically coupled to the same light pipe according to one exemplary embodiment of the invention.

Referring now to FIG. 8 which is an elevation view illustrating surface-mounted LED 235 and surface-mounted photodiode 240 both optically coupled to the same light pipe 140 according to one exemplary embodiment of the invention. Host system housing 110 encloses a light pipe 140 for optically coupling both LED 235 and photodiode 240 to the outside of the system housing 110. However, in other exemplary embodiments (not illustrated), the LED 235 and photodiode 240 may have separate light pipes 140 for propagating light into and out of the host system housing 110.

Light emitted from LED 235 is directed out through the outside surface 810 of the light pipe. Ambient light conditions outside the host system housing 110 may be directed from outside surface 810 of light pipe 140 into photodiode 240.

Both LED 235 and photodiode 240 are surface mounted to printed circuit board 830 where they are in electrical communication with ASI processor 210. Light pipe 140 may simplify system manufacture by enabling the use of surface mount components 235 and 240. An additional benefit of light pipe 140 may detect reflections off of surfaces beyond light pipe surface 810. ASI processor 210 may respond to the presence of these surfaces as an indication that the host system is enclosed and therefore slow or cease visual status indication.

Alternative embodiments of the environmentally responsive ASI system will become apparent to one of ordinary skill in the art to which the present invention pertains without departing from its spirit and scope. Thus, although this invention has been described in exemplary form with a certain degree of particularity, it should be understood that the present disclosure has been made only by way of example and that numerous changes in the details of construction and the combination and arrangement of parts or steps may be resorted to without departing from the spirit or scope of the invention. Accordingly, the scope of the present invention is defined by the appended claims rather than the foregoing description.

What is claimed is:

1. A status indicator system comprising:
   an indicator for communicating status of a defibrillator while the defibrillator is in a non-operative state;
   a sensor for measuring ambient environmental conditions of the defibrillator; and
   a controller for adjusting one of an intensity, a frequency and a duration of the indicator in response to the ambient environmental conditions measured by the sensor, wherein the controller communicates with the sensor to detect reflections produced by the indicator.

2. The status indicator system of claim 1, wherein the non-operative state comprises a non-rescue scenario of the defibrillator.

3. The status indicator system of claim 1, wherein the controller comprises a low-power sleep mode.

4. The status indicator system of claim 1, wherein the indicator comprises a light emitting element, the sensor comprises a light sensing element, and the controller comprises a circuit for adjusting brightness of the light emitting element.

5. The status indicator system of claim 1, wherein the indicator comprises a sound producing element, the sensor comprises a sound sensing element, and the controller comprises a circuit for adjusting a volume of the sound producing element.

6. The status indicator system of claim 1, wherein the defibrillator is portable.

7. The status indicator system of claim 1, wherein the reflections comprise light.

8. The status indicator system of claim 1, wherein the reflections comprise sound.

9. A method for adjusting power consumed by a status indicator system of a defibrillator based on ambient environmental conditions of the defibrillator comprising:
placing the defibrillator in an non-operative state;
detecting the ambient environmental conditions of the defibrillator;
measuring the detected ambient environmental conditions;
computing one of a frequency, an intensity, and a duration for the status indicator system coupled to the defibrillator;
activating the status indicator according to at least one of the frequency, the intensity, and the duration; and
sensing reflections of the indicator with a sensor.

10. The method of claim 9, further comprising removing power from the status indicator system after a predetermined period of time.

11. The method of claim 9, further comprising entering a low-power sleep state after activating the status indicator.

12. The method of claim 9, wherein detecting the ambient environmental conditions of the defibrillator comprises sensing ambient light levels, setting the intensity of the indicator system comprises adjusting the intensity of a light emitting element, and activating the status indicator comprises powering a light emitting element.

13. The method of claim 9, wherein detecting the ambient environmental conditions of the defibrillator comprises sensing ambient sound levels, setting the intensity of the status indicator system comprises adjusting a volume of a sound emitting element, and activating the status indicator system comprises powering a sound emitting element.

14. The method of claim 9, further comprising comparing the measured ambient environmental conditions to stored values.

15. A status indicator system comprising:
an light emitting diode for communicating status of a defibrillator;
a light sensor for measuring ambient light relative to a defibrillator; and
a controller for adjusting one of an intensity, a duration, and a frequency of the light emitting diode in response to the ambient lighting conditions measured by the light sensor, wherein the controller communicates with the light sensor to detect reflected light produced by the status indicator system.

16. The status indicator system of claim 15, wherein the light emitting diode and the light sensor are both optically coupled to a light pipe.

17. The status indicator system of claim 15, wherein the controller comprises a low-power sleep mode.

18. A status indicator system comprising:
an indicator for communicating status of a host system;
a sensor for measuring ambient environmental conditions of the host system while the host system is in a non-operative state; and
a controller for adjusting one of an intensity, a frequency, and a duration of the indicator in response to the ambient environmental conditions measured by the sensor, wherein the controller communicates with the sensor to detect reflections produced by the indicator.

19. The status indicator system of claim 18, wherein the controller comprises a low-power sleep mode.

20. The status indicator system of claim 18, wherein the indicator comprises a light emitting element, the sensor comprises a light sensing element, and the controller comprises a circuit for adjusting brightness of the light emitting element.

21. A status indicator system of claim 18, wherein the indicator comprises a sound producing element, the sensor comprises a sound sensing element, and the controller comprises a circuit for adjusting a volume of the sound producing element.

22. The status indicator system of claim 18, wherein the host system comprises a defibrillator.

23. The status indicator system of claim 18, wherein the reflections comprise light.

24. The status indicator system of claim 18, wherein the reflections comprise sound.

25. A method for adjusting power consumed by a status indicator system of a host device based on ambient environmental conditions of the host device comprising:
placing the host device in a non-operational state;
operating a processor of the status indicator system in a low-power standby mode;
detecting the ambient environmental conditions of the host device with a sensor, the conditions comprising reflections produced by the status indicator system; and
computing one of a frequency, an intensity, and a duration for the status indicator system coupled to the host device based on the ambient environmental conditions.

26. The method of claim 25, further comprising measuring the detected ambient environmental condition of the host device.

27. The method of claim 25, further comprising activating the status indicator according to at least one of the frequency, the intensity, and the duration.

28. The method of claim 25, further comprising returning the processor of the status indicator system to the low-power sleep mode after indicating status of the host device.

29. The method of claim 25, further comprising comparing the measured ambient environmental conditions to stored values.

* * * * *